United States Patent
Kondo et al.

(10) Patent No.: US 9,341,561 B2
(45) Date of Patent: May 17, 2016

(54) APERTURE ARRAY STRUCTURE AND MEASUREMENT METHOD USING THE SAME

(71) Applicant: MURATA MANUFACTURING CO., LTD., Nagaokakyo-Shi, Kyoto-Fu (JP)

(72) Inventors: Takashi Kondo, Nagaokakyo (JP); Seiji Kamba, Nagaokakyo (JP); Yuichi Ogawa, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 14/604,892

(22) Filed: Jan. 26, 2015

(65) Prior Publication Data

US 2015/0136989 A1    May 21, 2015

Related U.S. Application Data

(63) Continuation of application No. PCT/JP2013/068235, filed on Jul. 3, 2013.

(30) Foreign Application Priority Data

Jul. 27, 2012 (JP) ................................. 2012-166962

(51) Int. Cl.
*G01J 5/02*    (2006.01)
*G01N 21/01*    (2006.01)
*G01N 21/3586*    (2014.01)
(Continued)

(52) U.S. Cl.
CPC ............ *G01N 21/01* (2013.01); *G01N 21/3586* (2013.01); *G01N 21/47* (2013.01); *G02B 5/005* (2013.01); *G01N 2201/02* (2013.01); *G01N 2201/06113* (2013.01)

(58) Field of Classification Search
CPC .................................................. G01N 21/3586
See application file for complete search history.

(56) References Cited

U.S. PATENT DOCUMENTS

2012/0153159 A1    6/2012 Kamba et al.
2012/0235043 A1    9/2012 Ogawa et al.

FOREIGN PATENT DOCUMENTS

JP    2004-288240 A    10/2004
JP    2007-010366 A    1/2007
(Continued)

OTHER PUBLICATIONS

Hu et al., "Localized surface plasmons-based transmission enhancement of terahertz radiation through metal aperture arrays," 2010, Optik, vol. 121, pp. 1423-1426.*

(Continued)

*Primary Examiner* — Kiho Kim
(74) *Attorney, Agent, or Firm* — Arent Fox LLP

(57) ABSTRACT

An aperture array structure used in a method of measuring characteristics of a specimen by applying an electromagnetic wave to an aperture array structure on which the specimen is held, and detecting frequency characteristics of the electromagnetic wave scattered by the aperture array structure. The aperture array structure includes a first principal surface, a second principal surface opposed to the first principal surface, and a plurality of apertures extending through the aperture array structure in a direction perpendicular to the first principal surface and the second principal surface. An opening area of each aperture at the first principal surface is smaller than an opening area of each aperture at the second principal surface.

18 Claims, 4 Drawing Sheets

(51) Int. Cl.
  *G01N 21/47* (2006.01)
  *G02B 5/00* (2006.01)

(56) References Cited

FOREIGN PATENT DOCUMENTS

WO    WO-2008/093729 A1    8/2008
WO    WO-2011-027642 A1    3/2011

OTHER PUBLICATIONS

Nguyen et al., "Concentration of terahertz radiation through a conically tapered aperture,", 2010, Optics Express, vol. 18, No. 24, pp. 25441-25444.*

A. J. L. Adam, "Review of near-field terahertz measurement methods and their applications: How to actieve sub-wavelength resolution at THz frequencies," 2011, Journal of Infrared, Millimeters, Terahertz Waves, vol. 32, pp. 976-1019.*

Abbas et al., "New trends in instrumental design for surface plasmon resonance-based biosensors," 2011, Biosenss Bioelectron, vol. 26, No. 5, pp. 1825-1824.*

PCT/JP2013/068235 Copy of ISR dated Aug. 28, 2013.

PCT/JP2013/068235 Copy of Written Opinion dated Aug. 28, 2013.

Hitoshi Tabata; "High Sensitive Sensing for Bio, Medication and Food Related Materials by Terahertz Spectrum with Surface Wave Enhancement"; Bio Industry, vol. 27, No. 10, Oct. 12, 2010, pp. 38-47.

International Search Report issued for PCT/JP2013/068235, dated Sep. 10, 2013.

* cited by examiner

APERTURE ARRAY STRUCTURE AND MEASUREMENT METHOD USING THE SAME

CROSS REFERENCE TO RELATED APPLICATIONS

The present application is a continuation of International application No. PCT/JP2013/068235, filed Jul. 3, 2013, which claims priority to Japanese Patent Application No. 2012-166962, filed Jul. 27, 2012, the entire contents of each of which are incorporated herein by reference.

FIELD OF THE INVENTION

The present invention relates to an aperture array structure used for measurement of a specimen and a measurement method using the same.

BACKGROUND OF THE INVENTION

Hitherto, a measurement method has been used in which to analyze characteristics of a substance, a specimen is held on an aperture array structure, an electromagnetic wave is applied to the aperture array structure on which the specimen has been held, and a transmission spectrum or the like thereof is analyzed to detect characteristics of the specimen. A specific example thereof is a method of applying a terahertz wave to a specimen, such as a protein, attached to a metal mesh, and analyzing a transmission spectrum thereof.

As an existing technique which is such a method of analyzing a transmission spectrum using an electromagnetic wave, for example, Patent Document 1 (Japanese Unexamined Patent Application Publication No. 2007-010366) discloses a method of applying an electromagnetic wave toward an aperture array structure (e.g., a mesh-shaped conductive plate) on which a specimen has been held, measuring the electromagnetic wave having passed through the aperture array structure, and detecting characteristics of the specimen on the basis of a change in frequency characteristics of a measured value, the change being caused by the presence of the specimen.

In the aperture array structure disclosed in Patent Document 1, from the description of FIG. 18(b) and the like, the opening area of each aperture at the front side is basically substantially the same as that at the back side, the angle formed between an inner wall surface forming each aperture and a principal surface of the aperture array structure is assumed as substantially 90 degrees.

In such a case, if the amount of a specimen is small, a change in frequency characteristics is slight, and detection is difficult. Thus, provision of a measurement device for realizing measurement with excellent measurement sensitivity is still desired.

Patent Document 1: Japanese Unexamined Patent Application Publication No. 2007-010366

SUMMARY OF THE INVENTION

It is an object of the present invention to provide an aperture array structure for realizing measurement with more excellent measurement sensitivity than that in the related art, and a measurement method using the same.

In one aspect, the present invention is an aperture array structure used in a method of measuring characteristics of a specimen by applying an electromagnetic wave to an aperture array structure on which the specimen is held, and detecting frequency characteristics of the electromagnetic wave scattered by the aperture array structure, the aperture array structure comprising: a first principal surface; a second principal surface opposed to the first principal surface; and a plurality of apertures extending through the aperture array structure in a direction perpendicular to the first principal surface and the second principal surface, wherein an opening area of each aperture at the first principal surface is smaller than an opening area of each aperture at the second principal surface.

In the aperture array structure, an angle formed between the first principal surface of the aperture array structure and at least one inner wall of each aperture is preferably an acute angle.

In the aperture array structure, a ratio of the opening area of each aperture at the second principal surface relative to the opening area of each aperture at the first principal surface is preferably 1.02 to 2.5.

In the aperture array structure, an opening of each aperture at the first principal surface preferably has a size that does not allow the specimen to pass therethrough, and an opening of each aperture at the second principal surface preferably has a size that allows the specimen to pass therethrough.

In the aperture array structure, an inner wall of each aperture preferably also has a recess.

In another aspect, the present invention is a measurement method of measuring characteristics of a specimen by applying an electromagnetic wave to an aperture array structure on which the specimen is held, and detecting frequency characteristics of the electromagnetic wave scattered by the aperture array structure, the measurement method using the aperture array structure of the present invention.

In yet another aspect, the present invention is a measurement method of measuring characteristics of a specimen by applying an electromagnetic wave to an aperture array structure on which the specimen is held, and detecting frequency characteristics of the electromagnetic wave scattered by the aperture array structure, the measurement method using the aperture array structure of the present invention to hold the specimen near the first principal surface of the aperture array structure.

In another aspect, the present invention is a measurement method of measuring characteristics of a specimen by applying an electromagnetic wave to an aperture array structure on which the specimen is held, and detecting frequency characteristics of the electromagnetic wave scattered by the aperture array structure, the measurement method using the aperture array structure of the present invention to hold the specimen near the second principal surface of the aperture array structure.

In a further aspect, the present invention is a measurement method that uses the aperture array structure and moves the specimen from the second principal surface side of the aperture array structure in a direction to the first principal surface to hold the specimen at at least some of the apertures of the aperture array structure.

Since the aperture array structure according to the present invention includes apertures each having an opening area at the first principal surface smaller than an opening area at the second principal surface, an electromagnetic field concentrates on the vicinity of a portion where the first principal surface of the aperture array structure and the inner wall of each aperture are in contact with each other. As a result, a change in frequency characteristics of the detected electromagnetic wave which change is caused by presence/absence of a specimen in the vicinity of the portion where the first principal surface of the aperture array structure and the inner wall of each aperture are in contact with each other increases, and thus measurement sensitivity improves.

DETAILED DESCRIPTION OF THE PREFERRED EMBODIMENTS

Figure 1:
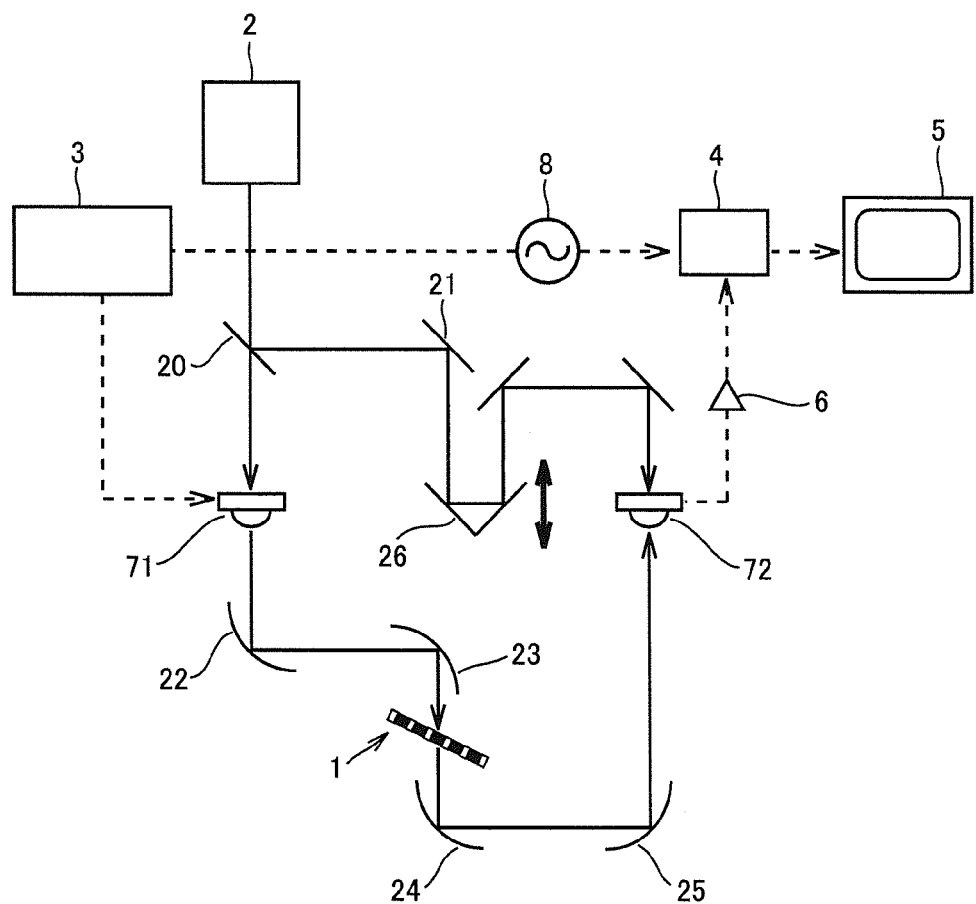
FIG. 1 is a schematic diagram for explaining an outline of a measurement method according to the present invention.

First, an outline of one example of a measurement method according to the present invention will be described with reference to FIG. 1. FIG. 1 is a diagram schematically showing the entire structure of one example of a measurement device used in the measurement method according to the present invention. The measurement device uses a pulse of an electromagnetic wave (e.g., a terahertz wave with a frequency of 20 GHz to 120 THz) generated by applying a laser beam from a laser 2 (e.g., a short pulse laser) to a semiconductor material.

In the configuration of FIG. 1, the laser beam emitted from the laser 2 is branched into two paths by a half mirror 20. One of the branched laser beams is applied to a photoconductive element 71 at the electromagnetic wave generation side, and the other laser beam is applied to a photoconductive element 72 at the reception side via a time delay stage 26 by using a plurality of mirrors 21 (reference numerals are omitted for other mirrors having the same function). As each of the photoconductive elements 71 and 72, a general photoconductive element is used which is obtained by forming, in LT-GaAs (low-temperature-grown GaAs), a dipole antenna having a gap portion. As the laser 2, a fiber laser or a laser using a solid such as titanium sapphire may be used. The electromagnetic wave may be generated and detected by using the surface of a semiconductor without an antenna, or by using an electro-optical crystal such as a ZnTe crystal. An appropriate bias voltage is applied from a power supply 3 to the gap portion of the photoconductive element 71 at the generation side.

The generated electromagnetic wave is converted to a parallel beam by a parabolic mirror 22 and is applied to an aperture array structure 1 by a parabolic mirror 23. The terahertz wave having passed through the aperture array structure 1 is received by the photoconductive element 72 via parabolic mirrors 24 and 25. An electromagnetic wave signal received by the photoconductive element 72 is amplified by an amplifier 6 and then obtained as a time waveform in a lock-in amplifier 4. The obtained time waveform is subjected to signal processing, such as Fourier transform, in a PC (personal computer) 5 including calculation means, and then a transmittance spectrum of the aperture array structure 1 and the like are calculated. To obtain the time waveform in the lock-in amplifier 4, the bias voltage applied from the power supply 3 to the gap of the photoconductive element 71 at the generation side is modulated (with an amplitude of 5 V to 30 V) by using a signal from an oscillator 8. With synchronous detection using the modulated voltage, it is possible to increase a signal to noise ratio.

The above-described measurement method is a method generally called terahertz time-domain spectroscopy (THz-TDS). A Fourier transform infrared spectroscopy (FT-IR) may be used instead of the THz-TDS.

FIG. 1 shows a case where scattering is transmission, that is, a case of measuring a transmittance of the electromagnetic wave. In the present invention, "scattering" means a broad concept including transmission which is one mode of forward scattering, reflection which is one mode of backward scattering, and the like, and is preferably transmission or reflection. Further preferably, scattering is transmission in a zero-order direction or reflection in the zero-order direction.

In general, where s indicates the grating space of a diffraction grating, i indicates an incident angle, $\theta$ indicates a diffraction angle, and $\lambda$ indicates a wave length, a spectrum diffracted by the diffraction grating can be represented as:

$$s(\sin i - \sin \theta) = n\lambda \quad (1).$$

The zero-order in the "zero-order direction" described above indicates a case where n in the above equation (1) is zero. Since s and $\lambda$ cannot be zero, n is zero only when $\sin i - \sin \theta = 0$. Accordingly, the "zero-order direction" described above indicates the direction in which the incident angle and the diffraction angle are the same, that is, the traveling direction of the electromagnetic wave does not change.

The electromagnetic wave used in the present invention is not particularly limited as long as it is an electromagnetic wave capable of causing scattering in response to the structure of the aperture array structure. Any of a radio wave, an infrared ray, a visible ray, an ultraviolet ray, an X-ray, a gamma ray, and the like may be used, and the frequency thereof is also not particularly limited but is preferably 1 GHz to 1 PHz, and the electromagnetic wave is more preferably a terahertz wave having a frequency of 20 GHz to 200 THz.

As the electromagnetic wave, a linearly polarized electromagnetic wave having a predetermined polarization direction (a linearly polarized wave) or an unpolarized electromagnetic wave (unpolarized wave) may be used. Examples of the linearly polarized electromagnetic wave include a terahertz wave generated by an optical rectification effect of an electrooptic crystal such as ZnTe with a short pulse laser as a light source, a visible ray emitted from a semiconductor laser, an electromagnetic wave radiated from a photoconductive antenna, and the like. Examples of the unpolarized electromagnetic wave include an infrared ray radiated from a high-pressure mercury lamp or a ceramic lamp, and the like.

In the present invention, measurement of presence/absence or an amount of a specimen is quantification of a compound that is the specimen. Examples thereof include measurement of the content of a very small quantity of the specimen in a solution or the like and identification of the specimen.

(Aperture Array Structure)

The aperture array structure according to the present invention has a first principal surface, a second principal surface opposed to the first principal surface, and a plurality of apertures extending therethrough in a direction perpendicular to the first principal surface and the second principal surface, and the opening area of each aperture on the first principal surface is smaller than the opening area of each aperture on the second principal surface.

For example, the plurality of apertures are arranged periodically in at least one direction on the principal surface of the aperture array structure. However, all of the apertures may be periodically arranged, or some of the apertures may be periodically arranged and the other apertures may be non-periodically arranged as long as the advantageous effects of the present invention are not impaired.

The aperture array structure is preferably a quasi-periodic structure or a periodic structure. The quasi-periodic structure is a structure that does not have translational symmetry but keeps order in array. Examples of the quasi-periodic structure include a Fibonacci structure as a one-dimensional quasi-periodic structure and a Penrose structure as a two-dimensional quasi-periodic structure. The periodic structure is a structure that has spatial symmetry, typified by translational symmetry, and is classified into a one-dimensional periodic structure, a two-dimensional periodic structure, and a three-dimensional periodic structure, depending on the dimension of the symmetry. Examples of the one-dimensional periodic structure include a wire-grid structure and a one-dimensional diffraction grating. Examples of the two-dimensional periodic structure include a mesh filter and a two-dimensional diffraction grating. Among these periodic structures, the two-dimensional periodic structure is preferably used.

Figure 2A:
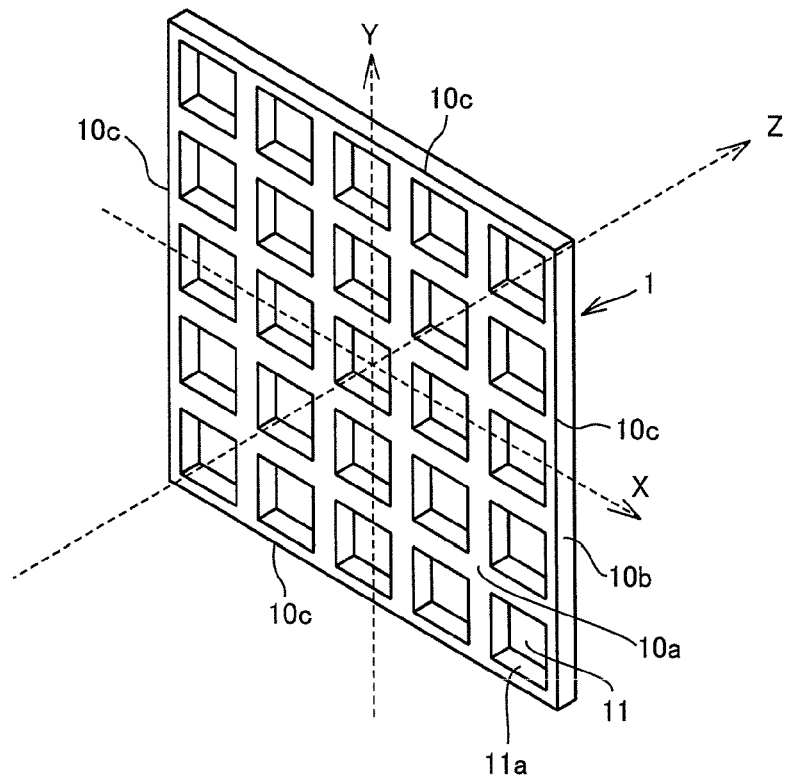
FIGS. 2(a) and 2(b) are schematic diagrams for explaining a structure of an aperture array structure used in the present invention.
Figure 2B:
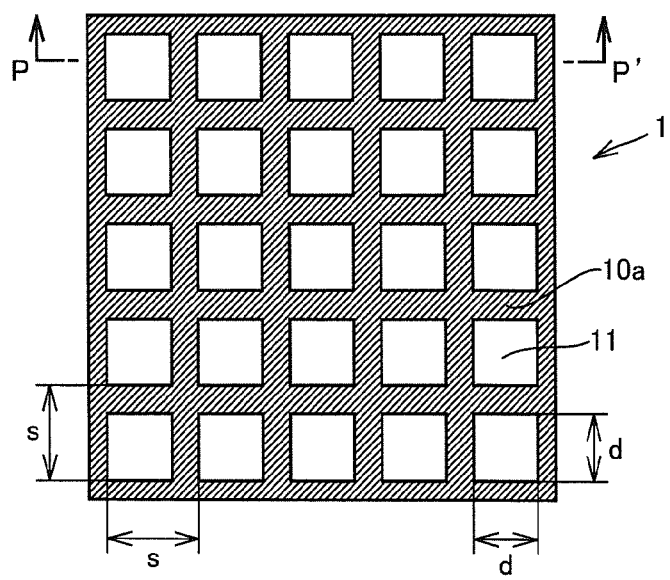

One example of the two-dimensional periodic structure is a plate-shaped structure (grating-shaped structure) shown in FIGS. 2(a) and 2(b), in which apertures are arranged at constant intervals in a matrix. The aperture array structure 1 shown in FIG. 2(a) is a plate-shaped structure in which apertures each having a square shape as seen from the principal surface 10a side thereof are spaced at equal intervals in two arrangement directions perpendicular to the respective sides of the square (vertically and laterally in the drawing).

Then angle formed between the first principal surface of the aperture array structure and at least one inner wall of each aperture is preferably an acute angle. Here, "at least one inner wall" means one of the surfaces forming the inner walls of the aperture. Therefore, a portion where the first principal surface of the aperture array structure and the inner wall intersects each other may be sharp, or R (a curved surface) may be formed at this portion. If R is formed, breakage or the like of this portion is suppressed, and it is possible to improve the strength of the aperture array structure.

The cross-sectional shape of each aperture on such a specific cross-section is not particularly limited, but examples thereof include a trapezoid and a shape that is generally a trapezoid. In other words, an example thereof is a shape in which the aperture widens from the first principal surface side (the side at which the opening area is small) toward the second principal surface side (the side at which the opening area is large) of the aperture array structure. The angle formed between the first principal surface of the aperture array structure and at least one inner wall of each aperture can be confirmed, for example, by observing a cross-section perpendicular to the principal surface of the aperture structure.

Figure 3:
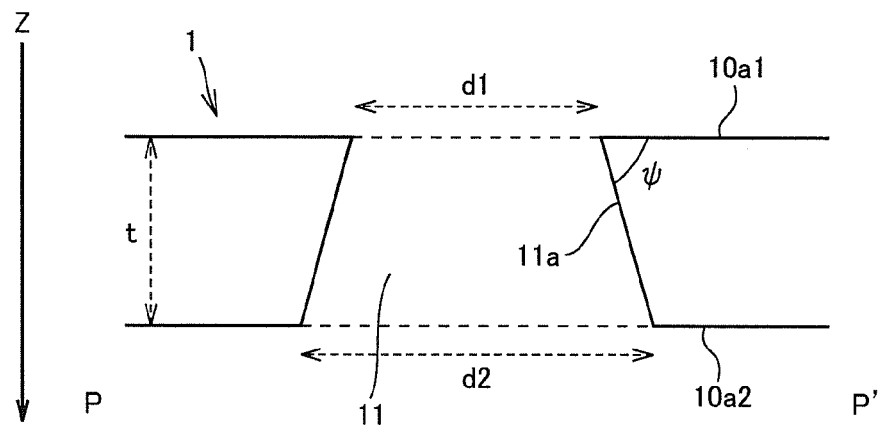
FIG. 3 is a schematic cross-sectional view taken along a P-P' cross-section in FIG. 2.

FIG. 3 shows a schematic cross-sectional view of one example of the aperture array structure according to the present invention as shown in FIGS. 2(a) and 2(b), taken along a P-P' cross-section in FIG. 2(b). As shown in FIG. 3, the cross-sectional shape of the aperture is substantially a trapezoid. A hole size d1 of the aperture 11 at the first principal surface of the aperture array structure 1 (the upper side in FIG. 3) is smaller than a hole size d2 of the aperture 11 at the second principal surface (the lower side in the drawing). That is, the opening area of the aperture 11 at the first principal surface 10a1 of the aperture array structure 1 is smaller than the opening area of the same aperture 11 at the second principal surface 10a2 of the aperture array structure 1.

The ratio (opening area ratio) of the opening area of the aperture at the second principal surface relative to the opening area of the aperture at the first principal surface is preferably 1.02 to 2.5. If the opening area ratio is increased, it is necessary to reduce the size of the opening in the first principal surface, and thus the transmittance of the entire aperture array structure for an electromagnetic wave is decreased. The decrease in transmittance leads to a decrease in measurement accuracy. Thus, in order to reduce a ratio of decrease in transmittance as a change amount to be about 10% or lower, it is necessary to make the opening area ratio to be not higher than 2.5. This relationship is obtained as follows. For example, for an aperture array structure in which the hole size at the first principal surface is 1.8 μm and the hole size at the second principal surface is 1.8 μm (1:1 as a ratio), where a maximum transmittance in a transmittance spectrum obtained when an electromagnetic wave is applied from a normal direction at the second principal surface side is defined as an initial value (100%), a relationship is analyzed between: the ratio (%), relative to the above initial value, of the similar maximum transmittance of the aperture array structure in which the hole size at the first principal surface is changed in a range of 1.3 to 1.8 μm and the hole size at the second principal surface is changed in a range of 1.8 to 2.3 μm; and the opening area ratio at that time. In addition, if the opening area ratio is less than 1.02, improvement of the measurement sensitivity is slight (within an error range), and the advantageous effects of the present invention are not obtained.

In addition, preferably, the opening of the aperture at the first principal surface has a size that does not allow a specimen to pass therethrough, and the opening of the aperture at the second principal surface has a size that allows a specimen to pass therethrough. In this case, when a specimen is moved (e.g., caused to flow) from the second principal surface side toward the first principal surface of the aperture array structure, the specimen is allowed to be held by at least a part of the apertures of the aperture array structure, and is allowed to be stably collected within the apertures and be measured.

In a cross-section (P-P' cross-section) perpendicular to the first principal surface 10a1 of the aperture array structure 1 shown in FIG. 3, the angle ψ formed between the first principal surface 10a1 of the aperture array structure 1 and an inner wall 11a of the aperture 11 is an acute angle.

In the case where each aperture 11 of the aperture array structure 1 has such a shape, it is possible to increase localization of an electromagnetic field of the applied electromagnetic wave near a portion where the first principal surface 10a1 of the aperture array structure 1 and the inner wall 11a of the aperture 11 are in contact with each other. As a result, a change in frequency characteristics of a detected electromagnetic wave which change is caused by presence/absence of a specimen near the portion where the first principal surface of the aperture array structure and the inner wall of the aperture are in contact with each other becomes great, and thus it is possible to improve the measurement sensitivity. That is, even when the amount of a specimen is small, measurement is possible with high sensitivity.

It should be noted that when a specimen is held near the second principal surface having a large opening area, measurement is performed in a region where leak of an electromagnetic field is great, and thus another advantage is obtained that it is made possible to also measure a larger specimen.

The inner wall 11a of the aperture 11 preferably has a recess. In other words, the inner wall 11a is preferably formed so as to draw a curved line that bulges outward of the aperture 11. Accordingly, it is made easier to collect a specimen within the aperture 11.

The dimensions and the arrangement of the apertures of the aperture array structure, the thickness of the aperture array structure, and the like are not particularly limited, and are set as appropriate in accordance with a measurement method, the material characteristics of the aperture array structure, the frequency of an electromagnetic wave to be used, and the like.

For example, in the aperture array structure 1 in which the apertures are regularly arranged vertically and horizontally as shown in FIG. 2(a), the hole size of each aperture which is indicated by d in FIG. 2(b) (the size of the opening at the side where the electromagnetic wave is applied) is preferably equal to or larger than one-tenth of the wave length of the electromagnetic wave used in measurement and equal to or smaller than 10 times that of this wave length. By so setting, the intensity of the electromagnetic wave scattered is increased, and it is made easier to detect a signal. Specifically, the hole size is preferably 0.15 to 150 μm, and in terms of improvement of the measurement sensitivity, the hole size is preferably 0.9 to 9 μm.

In addition, the opening area of the aperture at the side where the electromagnetic wave is applied is preferably 0.0225 to 22500 μm$^2$ and more preferably 0.81 to 81 μm$^2$.

In addition, in the aperture array structure 1 in which the apertures are regularly arranged vertically and horizontally as shown in FIG. 2(a), the grating space (pitch) between each aperture which is indicated by s in FIG. 2(b) is preferably equal to or smaller than one-tenth of the wave length of the electromagnetic wave used in measurement and equal to or larger than 10 times that of this wave length. By so setting, scattering more easily occurs. Specifically, the grating space is preferably 0.15 to 150 μm, and in terms of improvement of the measurement sensitivity, the grating space is preferably 1.3 to 13 μm.

Moreover, the thickness of the aperture array structure is preferably equal to or smaller than 5 times that of the wave length of the electromagnetic wave used in measurement. By so setting, the intensity of the electromagnetic wave scattered is increased, and it is made easier to detect a signal.

An optimum wave length of an electromagnetic wave to be applied (a wave length at which high measurement sensitivity is ensured) is different depending on the dielectric constant or the shape of a specimen. However, for example, when a specimen is a plate-shaped sample, in general, if the dielectric constant is the same, the optimum wave length of the electromagnetic wave to be applied tends to be shorter as the thickness of the specimen is decreased. Accordingly, when the grating space and the opening area of each aperture at the side where the electromagnetic wave is applied are decreased, it is possible to ensure high measurement sensitivity. In addition, for example, when the specimen is a particulate sample, in general, if the dielectric constant is the same, the optimum wave length of the electromagnetic wave to be applied tends to be shorter as the particle diameter of the specimen is decreased. Accordingly, when the grating space and the opening area of each aperture at the side where the electromagnetic wave is applied are decreased, it is possible to ensure high measurement sensitivity.

The dimension of the entire aperture array structure is not particularly limited, and is determined in accordance with the area of a beam spot of the electromagnetic wave to be applied, or the like.

At least a part of the surface of the aperture array structure is preferably formed of a conductor. At least a part of the surface of the aperture array structure 1 is a part of the surface of any one of a principal surface 10a, a side surface 10b, and the inner wall 11a of the aperture shown in FIG. 2(a).

The conductor refers to an object (substance) that conducts electricity, and not only a metal but also a semiconductor is included. Examples of the metal include a metal capable of bonding to a functional group of a compound having the functional group such as a hydroxy group, a thiol group, and a carboxyl group, a metal whose surface can be coated with a functional group such as a hydroxy group and an amino group, and an alloy of these metals. Specific examples thereof include gold, silver, copper, iron, nickel, chromium, silicon, germanium, and the like, and the metal is preferably gold, silver, copper, nickel, or chromium, and more preferably gold or nickel. In the case where gold or nickel is used, particularly, in the case where a host molecule has a thiol group (—SH group), it is advantageous since the host molecule can be bonded to the surface of the aperture array structure by using the thiol group. In the case where nickel is used, particularly, in the case where a host molecule has an alkoxylane group, it is advantageous since the host molecule can be bonded to the surface of the aperture array structure by using the alkoxylane group. Examples of the semiconductor include a compound semiconductor such as a group IV semiconductor (Si, Ge, and the like), a group II-VI semiconductor (ZnSe, CdS, ZnO, and the like), a group III-V semiconductor (GaAs, InP, GaN, and the like), a group IV compound semiconductor (SiC, SiGe, and the like), and a group I-III-VI semiconductor (CuInSe$_2$ and the like), and an organic semiconductor.

In the present invention, various publicly known methods may be used as a method of holding a specimen on the aperture array structure. For example, the specimen may be attached directly to the aperture array structure or may be attached thereto via a support film. In terms of performing measurement with reproducibility enhanced by improving the measurement sensitivity and suppressing variations in measurement, the specimen is preferably attached directly to the surface of the aperture array structure.

The cases where the specimen is attached directly to the aperture array structure include not only a case where a chemical bond or the like is directly formed between the surface of the aperture array structure and the specimen but also a case where the specimen is bound to a host molecule attached in advance to the surface of the aperture array structure. Examples of the chemical bond can include a covalent bond (e.g., a covalent bond between a metal and a thiol group) a Van der Waals bond, an ionic bond, a metallic bond, and a hydrogen bond. Preferably, the chemical bond is the covalent bond. The host molecule is a molecule to which the specimen can be specifically bound. Examples of a combination of the host molecule and the specimen include an antigen and an antibody, a sugar chain and a protein, a lipid and a protein, a low-molecular compound (ligand) and a protein, a protein and a protein, and a single-stranded DNA and a single-stranded DNA.

In the measurement method according to the present invention, characteristics of the specimen are measured on the basis of at least one parameter relating to the frequency characteristics of the scattered electromagnetic wave in the aperture array structure obtained as described above. For example, the characteristics of the specimen can be measured on the basis of a change in a dip waveform generated in the frequency characteristics of the electromagnetic wave forward-scattered (passing) through the aperture array structure 1 or a peak waveform generated in the frequency characteristics of the electromagnetic wave back-scattered (reflected) therefrom, the change being caused by the presence of the specimen.

The dip waveform is a waveform in a valley portion (convex downward) that partially appears in the frequency characteristics (e.g., a transmittance spectrum) of the aperture array structure in a frequency range where the ratio of a detected electromagnetic wave relative to an electromagnetic wave applied (e.g., the transmittance of the electromagnetic wave) relatively increases. The peak waveform is a mountain shaped (upward convex) waveform that partially appears in the frequency characteristics (e.g., a reflectance spectrum) of the aperture array structure in a frequency range where the ratio of a detected electromagnetic wave relative to an electromagnetic wave applied (e.g., the reflectance of the electromagnetic wave) decreases.

EXAMPLES

The present invention will be described in further detail below by means of examples, but the present invention is not limited to them.

Example 1

An aperture array structure having a square grating arrangement with square holes as shown in FIGS. 2(a) and 2(b) was used as an aperture array structure. The grating space is 260 μm (s), and the thickness is 60 μm (t). In addition, regarding the shape of each aperture in the aperture array structure, as shown in FIG. 3, the cross-sectional shape of each aperture in the P-P' cross-section in FIG. 2(b) is substantially a trapezoid. The hole size d1 at the first principal surface 10a1 side was 160 μm, and the hole size d2 at the second principal surface 10a2 side was 200 μm.

A parallel plate sample (specimen) having a film thickness of 4 μm, a real part of a complex index of refraction of 1.55, and an imaginary part of the complex index of refraction of 0 was brought into close contact with the first principal surface 10a1 side of the aperture array structure 1, an electromagnetic wave was applied from the first principal surface 10a1 side (the arrow direction of a Z axis in FIG. 3), and a transmittance spectrum of the electromagnetic wave was calculated.

Figure 4:
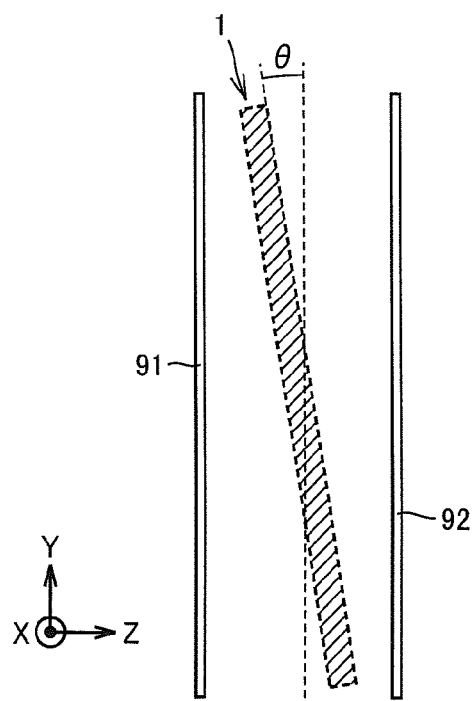
FIG. 4 is a schematic diagram showing an installed of an aperture array structure according to Example 1 is.

The calculation was performed by using an electromagnetic field simulator (Microstripes: manufactured by CST) for a model (see FIG. 4) in which the aperture array structure 1 was provided between two ports 91 and 92 spaced apart from each other at an interval of 600 μm. Polarization of the electromagnetic wave to be applied to the aperture array structure 1 was linear polarization (parallel to a Y axis in FIG. 2(a)), and the travelling direction thereof was the arrow direction of the Z axis. In addition, the aperture array structure 1 was positioned such that the principal surface thereof was perpendicular to the travelling direction of the electromagnetic wave (the Z axis direction) (i.e., such that θ in FIG. 4 was 0 degree).

Figure 5:
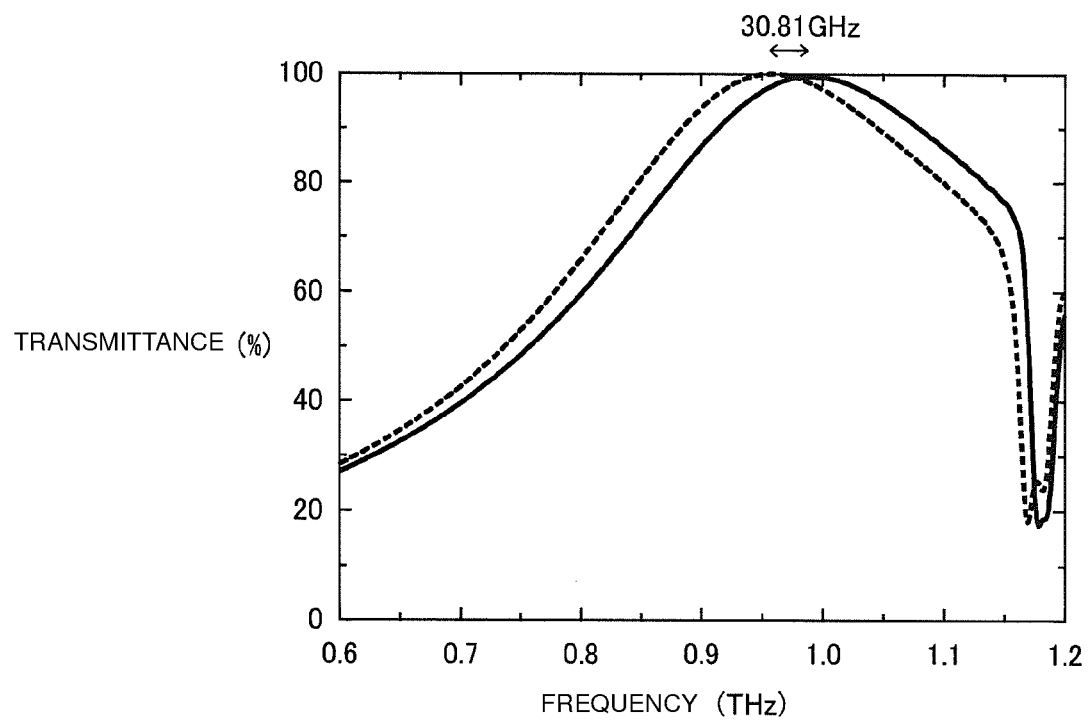
FIG. 5 is a diagram showing a transmission spectrum obtained in Example 1.

FIG. 5 shows transmittance spectra obtained through the calculation. In FIG. 5, a solid line denotes a transmittance spectrum obtained when no specimen was held on the aperture array structure, and a broken line denotes a transmittance spectrum obtained when the specimen was held on the aperture array structure. In FIG. 5, the difference (frequency shift amount) between frequencies at which peaks appeared in the transmittance spectra was 30.81 GHz.

Comparative Example 1

As Comparative Example 1, for a case where the hole size d1 at the first principal surface 10a1 side of the aperture array structure 1 and the hole size d2 at the second principal surface 10a2 side of the aperture array structure 1 were the same (a case where d1=d2: a case where a cross-sectional shape of each aperture was a rectangular), a transmittance spectrum was calculated by using an electromagnetic field simulator, similarly to Example 1. Transmittance spectra in the case where no specimen was held and the case where a specimen was held in three cases, namely, in the case where each of d1 and d2 was 160 μm, in the case where each of d1 and d2 was 180 μm, in the case where each of d1 and d2 was 200 μm were calculated, and frequency shift amounts thereamong were obtained.

As a result, the frequency shift amount in the case where each of d1 and d2 was 160 μm was 29.00 GHz, the frequency shift amount in the case where each of d1 and d2 was 180 μm was 29.91 GHz, and the frequency shift amount in the case where each of d1 and d2 was 200 μm was 28.09 GHz.

From the results of Example 1 and Comparative Example 1, it is understood that since the opening area at the first principal surface and the opening area at the second principal surface of the aperture array structure were different from each other, the frequency shift amount increased and the measurement sensitivity improved. In addition, from the results of Example 1 and Comparative Example 1, it is understood that since the angle formed between the first principal surface of the aperture array structure and the inner wall of each aperture was an acute angle, the frequency shift amount increased and the measurement sensitivity improved.

The embodiment and Example disclosed this time are illustrative in all points and should be considered as not restrictive. The scope of the present invention is shown not by the above description but by the scope of claims, and it is intended that all modifications within the meaning and scope equivalent to the scope of claims are included.

REFERENCE SIGNS LIST 1 aperture array structure
10a principal surface
10a1 first principal surface
10a2 second principal surface
10b side surface
10c outer periphery
11 aperture
11a inner wall
2 laser
20 half mirror
21 mirror
22, 23, 24, 25 parabolic mirror
26 time delay stage
3 power supply
4 lock-in amplifier
5 PC (personal computer)
6 amplifier
71, 72 photoconductive element
8 oscillator
91, 92 port

The invention claimed is:
1. An aperture array structure comprising:
a first principal surface;
a second principal surface opposed to the first principal surface; and
a plurality of apertures extending through the aperture array structure in a direction perpendicular to the first principal surface and the second principal surface, wherein
a first opening area of each aperture at the first principal surface is smaller than a second opening area of each aperture at the second principal surface, and
an inner wall of each aperture has a recess.
2. The aperture array structure according to claim 1, wherein an angle between the first principal surface of the aperture array structure and at least one inner wall of each aperture is an acute angle.
3. A method of measuring characteristics of a specimen, the method comprising:

applying an electromagnetic wave to an aperture array structure according to claim 2 on which the specimen is held near the first principal surface of the aperture array structure; and detecting frequency characteristics of the electromagnetic wave scattered by the aperture array structure.

4. A method of measuring characteristics of a specimen, the method comprising:

applying an electromagnetic wave to an aperture array structure according to claim 2 on which the specimen is held near the second principal surface of the aperture array structure; and detecting frequency characteristics of the electromagnetic wave scattered by the aperture array structure.

5. The aperture array structure according to claim 1, wherein a ratio of the second opening area of each aperture at the second principal surface relative to the first opening area of each aperture at the first principal surface is 1.02 to 2.5.

6. The aperture array structure according to claim 1, wherein the first opening area of each aperture at the first principal surface has a size that does not allow a specimen to pass therethrough, and the second opening area of each aperture at the second principal surface has a size that allows the specimen to pass therethrough.

7. A measurement method comprising:

using the aperture array structure according to claim 6 and moving the specimen from the second principal surface side of the aperture array structure toward the first principal surface so that the specimen is held by at least some of the apertures of the aperture array structure.

8. The aperture array structure according to claim 1, wherein the aperture array structure is a periodic structure.

9. The aperture array structure according to claim 1, wherein a cross-sectional shape of each aperture is trapezoidal.

10. The aperture array structure according to claim 1, wherein a hole size of each aperture on a side thereof upon which an electromagnetic wave is applied for measuring characteristics of a specimen is equal to or larger than one-tenth of a wave length of the electromagnetic wave and equal to or smaller than 10 times the wave length.

11. The aperture array structure according to claim 10, wherein the hole size is 0.15 to 150 µm.

12. The aperture array structure according to claim 10, wherein the hole size is 0.9 to 9 µm.

13. The aperture array structure according to claim 10, wherein the opening area of the aperture at the side where the electromagnetic wave is applied is 0.0225 to 22500 µm$^2$.

14. The aperture array structure according to claim 10, wherein the opening area of the aperture at the side where the electromagnetic wave is applied is 0.81 to 81 µm$^2$.

15. The aperture array structure according to claim 1, wherein a grating space between each aperture is equal to or smaller than one-tenth of a wave length of an electromagnetic wave used in measurement and equal to or larger than 10 times the wave length.

16. The aperture array structure according to claim 15, wherein the grating space is 0.15 to 150 µm.

17. The aperture array structure according to claim 15, wherein, the grating space is 1.3 to 13 µm.

18. A method of measuring characteristics of a specimen, the method comprising:

applying an electromagnetic wave to an aperture array structure according to claim 1 on which the specimen is held; and detecting frequency characteristics of the electromagnetic wave scattered by the aperture array structure.

* * * * *